United States Patent [19]

Bittler et al.

[11] Patent Number: 4,868,166
[45] Date of Patent: Sep. 19, 1989

[54] 2,2:6,6-DIETHYLEN-3-OXO-17ALPHA-PREGN-4-ENE-21,17ALPHA-CARBOLACTONES, PROCESS FOR THEIR PRODUCTION & PHARMACEUTICAL PREPARATIONS CONTAINING THEM

[75] Inventors: Dieter Bittler; Klaus Nickisch; Henry Laurent; Rudolf Wiechert; Martin Haberey, all of Berlin, Fed. Rep. of Germany

[73] Assignee: Schering Aktiengesellschaft, Berlin and Bergkamen, Fed. Rep. of Germany

[21] Appl. No.: 150,413

[22] PCT Filed: May 5, 1987

[86] PCT No.: PCT/DE87/00208
§ 371 Date: Feb. 5, 1988
§ 102(e) Date: Feb. 5, 1988

[87] PCT Pub. No.: WO87/06937
PCT Pub. Date: Nov. 19, 1987

[30] Foreign Application Priority Data
May 7, 1986 [DE] Fed. Rep. of Germany ....... 3615376

[51] Int. Cl.$^4$ .......... A61K 31/58; C07J 21/00; C07J 19/00
[52] U.S. Cl. ....................... 514/173; 540/8; 540/11
[58] Field of Search ............... 514/173; 540/8, 11

[56] References Cited

U.S. PATENT DOCUMENTS 3,422,097  1/1969  Kerwin ................... 540/8
4,584,288  4/1986  Nickish et al. .......... 540/8

OTHER PUBLICATIONS

Chemical Abstracts, vol. 103 (1985) #215646w; Sandor et al.

*Primary Examiner*—Douglas W. Robinson
*Assistant Examiner*—Joseph A. Lipovsky
*Attorney, Agent, or Firm*—Millen, White & Zelano

[57] ABSTRACT

2,2;6,6-diethylene-3-oxo-17alpha-pregn-4-ene-21,17-carbolactones of general formula I,

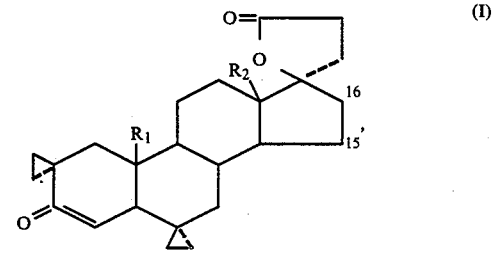

wherein
$R_1$ represents a hydrogen atom or a methyl group,
$R_2$ represents a methyl or ethyl group and

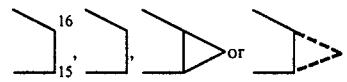

process for their production and their pharmaceutical use.

7 Claims, No Drawings

2,2:6,6-DIETHYLEN-3-OXO-17ALPHA-PREGN-4-ENE-21,17ALPHA-CARBOLACTONES, PROCESS FOR THEIR PRODUCTION & PHARMACEUTICAL PREPARATIONS CONTAINING THEM

The invention relates to 2,2;6,6-diethylene-3-oxo-17alpha-pregn-4-ene-21,17alpha-carbolactones of general formula I, process for their production and pharmaceutical preparations containing them as mentioned in the claims.

For the treatment of certain forms of hypertension, edemas, primary aldosteronism and other endocrinological disorders caused by aldosterone and as diuretics, substances are used which reverse the effect of aldosterone or desoxycorticosterone on the sodium and potassium salt elimination and whose best known representative is spironolactone long available as a commercial product. But in the treatment with spironolactone undesirable endocrine side effects often occur, which are caused by the antiandrogen and gestagen activity of spironolactone. Thus in the case of prolonged continuous treatment of male patients with spironolactone the occurrence of gynecomastia (Smith, W. G., The Lancet 1962, p. 886; Mann, N. M., JAMA 1963, p. 778; Clark, E., JAMA 1965, p. 157; Greenblatt, D. J., JAMA 1973, p. 82) and impotence (Greenblatt, D. J., JAMA 1973, p. 82), is observed which is ascribed to the antiandrogen side effect of this active ingredient (Steelman, S. L. et al, Steroids 1963, p. 449; Schane, H. P., J. of Clinical Endocrinology and Metabolism 1978, p. 691).

On the other hand, side effects such as amenorrhea and menstrual irregularities occurring in women being treated with spironolactone are blamed on the gestagen side effect of spironolactone. Both side effects can be proven both in animal tests and in vitro by the receptor binding test with the androgen or gestagen receptor. Spirorenone, superior to spironolactoe in its antialdosterone effect, also binds relatively strongly to the gestagen receptor.

The object of this invention was to make available compounds which are superior to spirorenone in antialdosterone effect but have a greatly reduced gestagen side effect.

6,6-ethylene-15,16-methylene-3-oxo-17alpha-pregn-4-ene-21,17-carbolactones, which have both an aldosterone antagonist and a gestagen effect, are known from German laid-open specification No. 34 02 329.

The new compounds of general formula I exhibit a marked increase of the antimineral corticoid effect. The affinity of the new compounds for the gestagen receptor is considerably reduced by the additional cyclopropyl ring in the 2 position (the competition factor is greater than 20). In comparison with spirorenone the new compounds prove to be suitable antimineral corticoids with up to 50% better aldosterone antagonist effect and up to 10 times less affinity for the gestagen receptor (in comparison with dihydrospirorenone, the active metabolite of spirorenone).

The relative values of the strength of action of antialdosterone and the competition factors in the gestagen receptor test (KG) of spirorenone (A) and the compounds according to the invention in the example of 2,2;6,6-diethylene-18-methyl-15beta,16beta-methylene-3-oxo-19-nor-17alpha-pregn-4-ene-21,17-carbolactone (B) are compiled in the following table.

Formulation of the pharmaceutical preparations on the basis of the new compounds takes place in a way known in the art by processing the active ingredient with vehicles, diluents, optionally taste corrigents, etc., usual in galenics and transforming them into the desired application form.

Especially tablets, dragees, capsules, pills, suspensions or solutions are suitable for the preferred oral application.

Especially oily solutions, such as, for example, solutions in sesame oil, castor oil and cottonseed oil are suitable for parenteral application. Solubilizing agents such as, for example, benzyl benzoate or benzyl alcohol, can be used to increase solubility.

Production of the compounds of general formula I according to the invention takes place according to claim 6.

First the delta$^4$-3-ketone is transformed with a secondary base into the corresponding delta$^{3,5}$-3-amine.

Diethylamine, aniline, pyrrolidine and morpholine, for example, are suitable as secondary bases.

For introduction of the hydroxymethyl groups in the 2,6 position the delta$^{3,5}$-3-amine is treated with formalin in alcoholic solution.

The corresponding 2,6-disulfonyloxy compound is produced from the 2,6-dihydroxymethyl compound with an alkane or arene sulfonyl chloride in the presence of a tert-base such as triethylamine in $CH_2Cl_2$.

Methylenation of this compound to the 2,2;6,6-diethylene compound takes place with dimethyl sulfoxonium methylide. For this purpose, the 6-methylene steroid is added to a suspension of trimethyl sulfoxonium iodide with sodium hydride in mineral oil and dimethyl sulfoxide or to a solution of trimethyl sulfoxonium iodide and sodium hydroxide in dimethyl sulfoxide. The reaction is ended after 15 to 60 minutes at 20°–40° C.

EXAMPLE 1

(a) A solution of 3.85 g of 18-methyl-15beta,16beta-methylene-3-oxo-19-nor-17alpha-pregn-4-ene-21,17-carbolactone in 77 ml of methanol is refluxed with 1.93 ml of pyrrolidine for 15 minutes. After cooling in an ice bath the precipitate was suctioned off, washed with a little methanol and dried. 3.75 g of 18-methyl-15beta,16beta-methylene-3-pyrrolidino-19-nor-17alpha-pregna-3,5-diene-21,17-carbolactone is obtained.

UV: epsilon$_{276}$=23,000.

(b) A solution of 3.75 ml of 37% formalin solution in 60 ml of ethanol is instilled in a suspension of 3.75 g of 18-methyl-15beta,16beta-methylene-3-pyrrolidino-19-nor-17alpha-pregna-3,5-diene-21,17-carbolactone in 60 ml of toluene within 30 minutes at room temperature. After a reaction time of 30 minutes the reaction solution is evaporated in a vacuum to dryness. The residue is chromatographed on silica gel and 800 mg of 2beta,6beta-dihydroxymethyl-18-methyl-15beta,16beta-methylene-3-oxo-19-nor-17alpha-pregn-4-ene-21,17-carbolactone is obtained as oil.

UV: epsilon$_{243}$=13,400.

(c) 800 mg of 2beta,6beta-dihydroxymethyl-18-methyl-15beta,16beta-methylene-3-oxo-19-nor-17alpha-pregn-4-ene-21,17-carbolactone is dissolved in 8 ml of dichloromethane and cooled in an ice bath. Then 1.25 ml of triethylamine and 0.475 ml of methane sulfonic acid chloride are added, stirred for 45 minutes with cooling, then mixed with 0.225 ml of water and stirred for 30 more minutes. The reaction solution is diluted with ether, washed with water, dried over sodium sulfate and evaporated. 1.1 g of 2beta,6beta-dimesyloxymethyl-18-methyl-15beta,16beta-methylene-3-oxo-19-nor-17alpha-pregn-4-ene-21,17-carbolactone is obtained as oil.

(d) 3.46 g of trimethyl sulfoxonium iodide is stirred with 573 mg of sodium hydride (55% oil suspension) in 66 ml of dimethyl sulfoxide for 1.5 hour at room temperature. To this solution is added under argon 1.1 g of 2beta,6beta-dimesyloxy-18-methyl-15beta,16beta-methylene-3-oxo-19-nor-17alpha-pregn-4-ene-21,17-carbolactone, then it is stirred for 1 hour at room temperature. The reaction solution is diluted with ether, washed with water, dried and evaporated. The residue is chromatographed on silica gel and, after trituration with diisopropyl ether 200 mg of 2,2;6,6-diethylene-18-methyl-15beta,16beta-methylene-3-oxo-19-nor-17alpha-pregn-4-ene-21,17-carbolactone with a melting point of 213.7° C. is obtained.

UV: epsilon$_{251}$=14,200.

EXAMPLE 2

(A) 5.0 g of 15beta,16beta-methylene-3-oxo-17alpha-pregn-4-ene-21,17-carbolactone is reacted in 37.5 ml of methanol with 2.5 ml of pyrrolidine, as described in example 1(a) and worked up. 5.1 g of 15beta,16beta-methylene-3-pyrrolidino-17alpha-pregna-3,5-diene-21,17-carbolactone with a melting point of 236°-238° C. (with decomposition) is obtained.

(b) 5.1 g of 15beta,16beta-methylene-3-pyrrolidino-17alpha-pregna-3,5-diene-21,17-carbolactone is reacted in 51 ml of benzene and 102 ml of ethanol with 5.1 ml of 37% formalin solution, as described in example 1(b), and worked up. After chromatography on silica gel, 1.02 g of 2beta, 6beta-dihydroxymethyl-15beta,16beta-methylene-3-oxo-17alpha-pregn-4-ene-21,17-carbolactone is obtained as oil.

UV: epsilon$_{242}$=12,600

(c) 1.02 g of 2beta,6beta-dihydroxymethyl-15beta,16beta-methylene-3-oxo-17alpha-pregn-4-ene-21,17-carbolactone is allowed to stand in 10 ml of pyridine with 1.4 g of p-toluenesulfonic acid chloride for 16 hours at room temperature. Then 0.132 ml of water is added, it is stirred for 1 hour at room temperature and the reaction solution is stirred into ice water. The precipitate is filtered off, washed with water and dissolved in methylene chloride. The organic phase is washed with water, dried and evaporated. 1.06 g of oily 15beta,16beta-methylene-3-oxo-2beta,6beta-ditosyloxy-17alpha-pregn-4-ene-21,17-carbolactone is obtained as residue.

(d) 1.04 g of 15beta,16beta-methylene-3-oxo-2beta,6beta-ditosyloxy-17alpha-pregn-4-ene-21,17-carbolactone is reacted in 50 ml of dimethyl sulfoxide with 2.61 g of trimethylsulfoxonium iodide and 432 mg of sodium hydride (55% oil suspension), as described in example 1(d), and worked up. After chromatography on silica gel and diisopropylether trituration 245 mg of 2,2;6,6-diethylene-15beta,16beta-methylene-3-oxo-17alpha-pregn-4-ene-21,17-carbolactone with a melting point of 229° C. is obtained.

UV: epsilon252=13,100.

EXAMPLE 3

(a) 6 ml of pyrrolidine is added to a solution of 12.0 g of 15beta,16beta-methylene-19-nor-3-oxo-17alpha-pregn-4-ene-21,17-carbolactone in 100 ml of methanol and refluxed for 20 minutes. After cooling, the precipitate is suctioned off, washed with a little cold methanol and dried in a vacuum. 13.2 g of 15beta,16beta-methylene-19-nor-3-pyrrolidino-17alpha-pregna-3,5-diene-21,17-carbolactone is obtained.

(b) 20 ml of 37% formalin solution in 200 ml of ethanol is instilled in a solution of 13.0 g of 15beta,16beta-methylene-19-nor-3-pyrrolidino-17alpha-pregna-3,5-diene-21,17-carbolactone in 200 ml of toluene within 1 hour at room temperature. After a reaction time of 30 minutes, the reaction solution is evaporated to dryness in a vacuum. The resulting residue is chromatographed on silica gel. 2.6 g of 2beta,6beta-dihydroxymethyl-15beta,16beta-methylene-3-oxo-19-nor-17alpha-pregn-4-ene-21,17-carbolactone is obtained at oil.

UV: epsilon$_{242}$=12,950

(c) A solution of 2.5 g of 2beta,6beta-dihydroxymethyl-15beta,16beta-methylene-3-oxo-19-nor-17alpha-pregn-4-ene-21,17-carbolactone in 25 ml of abs. dichloromethane is mixed with 4 ml of triethylamine and 1.5 ml of methanesulfonic acid chloride with ice cooling and restirred for 30 minutes. Then it is mixed with 1 ml of water and stirred for 30 more minutes. The reaction solution is then diluted with ether, washed with water, dried over sodium sulfate and evaporated in a vacuum. 3.05 g of 2beta,6beta-dimesyloxymethyl-15beta,16beta-methylene-3-oxo-19-nor-17alpha-pregn-4-ene-21,17-carbolactone is obtained as oil.

(d) A solution of 10.5 g of trimethylsulfoxonium iodide is 100 ml of DMSO is mixed with 1.7 g of sodium hydride (55% oil suspension) and stirred for 1.5 hours at room temperature. 3.0 g of 2beta,6beta-dimesyloxymethyl-15beta,16beta-methylene-3-oxo-19-nor-17alpha-pregn-4-ene-21,17-carbolactone in 25 ml of DMSO is added to this solution and restirred for 1 hour. The reaction solution is diluted with ether, washed with water, dried and evaporated in a vacuum. The residue is chromatographed on silica gel. 720 mg of 2,2;6,6-diethylene-15beta,16beta-methylene-3-oxo-19-nor-17alpha-pregn-4-ene-21,17-carbolactone is obtained.

UV: epsilon$_{252}$=14,705.

TABLE

| Compound | Relative antialdosterone effect | Competition factor K$_G$ |
| --- | --- | --- |
| A | 1 | 2.7 |
| B | 1.5 | 20 |

The test models are described in detail in DE-OS Nos. 3227598 and 3402329.

We claim:

1. A 2,2;6,6-diethlylene-3oxo-17alpha-pregn-4-ene-21,17-carbolactone of general formula I,

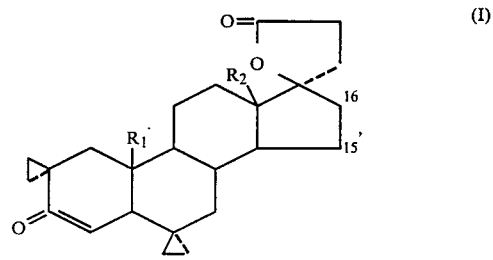

(I)

wherein

R$_1$ represents a hydrogen atom or a methyl group
R$_2$ represents a methyl or ethyl group and

2. A pharmaceutical composition comprising a compound of claim 1 and a pharmaceutically acceptable carrier.

3. A method for achieving an anti-aldosterone effect comprising administering an effective amount of a compound of claim 1 to a patient in need thereof.

4. A method of claim 3 wherein the anti-aldosterone effect is related to a reduction of hypertension, edema or primary aldosteronism.

5. 2,2;6,6-diethylene-18-methyl-15beta,16beta-methylene-3-oxo-19-nor-17alpha-pregn-4-ene-21,17-carbolactone a compound of claim 1.

6. 2,2;6,6-diethylene-15beta,16-beta-methylene-3oxo-17alpha-pregn-4-ene-21,17-carbolactone a compound of claim 1.

7. 2,2;6,6-diethylene-15beta,16,beta-methylene-3-oxo-19-nor-17alpha-pregn-4-ene-21,17-carbolactone a compound of claim 1.

* * * * *

UNITED STATES PATENT AND TRADEMARK OFFICE
CERTIFICATE OF CORRECTION

PATENT NO. : 4,868,166
DATED : 09/19/89
INVENTOR(S) : BITTLER et al.

It is certified that error appears in the above-identified patent and that said Letters Patent is hereby corrected as shown below: Col. 4, the Formula in Claim 1, should read --

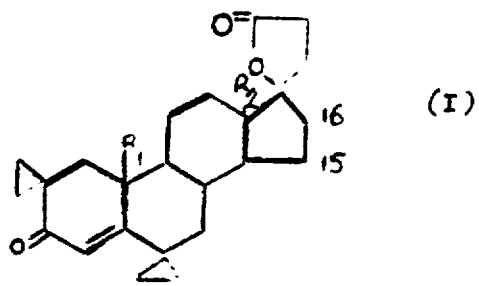

Signed and Sealed this

Eighth Day of September, 1992

*Attest:*

DOUGLAS B. COMER

*Attesting Officer*   Acting Commissioner of Patents and Trademarks